(12) United States Patent
Hu et al.

(10) Patent No.: US 11,439,373 B2
(45) Date of Patent: Sep. 13, 2022

(54) ENDOSCOPIC REUSABLE SURGICAL DEVICE

(71) Applicant: Covidien LP, Mansfield, MA (US)

(72) Inventors: Encheng Hu, Shanghai (CN); Xiaolin Sang, Shanghai (CN); Xin Yue, Shanghai (CN)

(73) Assignee: Covidien LP, Mansfield, MA (US)

( * ) Notice: Subject to any disclaimer, the term of this patent is extended or adjusted under 35 U.S.C. 154(b) by 468 days.

(21) Appl. No.: 16/485,501

(22) PCT Filed: Mar. 20, 2017

(86) PCT No.: PCT/CN2017/077303
§ 371 (c)(1),
(2) Date: Aug. 13, 2019

(87) PCT Pub. No.: WO2018/170680
PCT Pub. Date: Sep. 27, 2018

(65) Prior Publication Data
US 2020/0046334 A1  Feb. 13, 2020

(51) Int. Cl.
*A61L 9/00* (2006.01)
*A61L 2/00* (2006.01)
(Continued)

(52) U.S. Cl.
CPC ........ *A61B 17/00234* (2013.01); *A61L 2/186* (2013.01); *A61B 17/29* (2013.01);
(Continued)

(58) Field of Classification Search
CPC ... A61B 1/0057; A61B 1/0055; A61B 1/0052; A61B 1/008; A61L 2/0088; A61L 2/18; A61L 2202/24
(Continued)

(56) References Cited

U.S. PATENT DOCUMENTS

| 5,344,428 A | 9/1994 | Griffiths | |
|---|---|---|---|
| 2010/0049001 A1* | 2/2010 | Yamane | A61B 1/00068 600/159 |
| 2015/0173589 A1* | 6/2015 | Mitchell | A61M 25/0147 600/142 |

FOREIGN PATENT DOCUMENTS

| CN | 204293107 U | 4/2015 |
|---|---|---|
| DE | 29602064 U1 | 3/1997 |

(Continued)

OTHER PUBLICATIONS

Supplementary European Search Report dated Oct. 28, 2020 issued in corresponding EP Appln. No. 17901913.8.
(Continued)

*Primary Examiner* — Monzer R Chorbaji
(74) *Attorney, Agent, or Firm* — Carter, DeLuca & Farrell LLP

(57) ABSTRACT

An endoscopic shaft assembly includes: an elongate outer shaft; and an outer housing coupled to a proximal portion of the elongate outer shaft. The outer housing includes: a tubular wall defining a cavity; and a shaft plunger disposed within the cavity and configured to move axially within at least a portion of the cavity along a travel path. The shaft plunger includes a collar. The collar is configured to be separated from the tubular wall along a first travel portion of the travel path and to contact the tubular wall along a second travel portion of the travel path.

19 Claims, 5 Drawing Sheets

(51) Int. Cl.
  *A61B 1/00*     (2006.01)
  *A61B 1/12*     (2006.01)
  *A61B 1/267*    (2006.01)
  *A61B 17/00*    (2006.01)
  *A61L 2/18*     (2006.01)
  *A61B 17/29*    (2006.01)
  *A61B 90/70*    (2016.01)

(52) U.S. Cl.
  CPC ....... *A61B 90/70* (2016.02); *A61B 2017/0046* (2013.01); *A61L 2202/24* (2013.01)

(58) Field of Classification Search
  USPC ...................... 422/28, 32, 292, 300; 600/159
  See application file for complete search history.

(56) References Cited

FOREIGN PATENT DOCUMENTS

| | | | |
|---|---|---|---|
| JP | 2010259565 A | 11/2010 | |
| JP | 2012125401 A | 7/2012 | |
| WO | 2016197350 A1 | 12/2016 | |

OTHER PUBLICATIONS

International Search Report for PCT/CN2017/077303 date of completion is Nov. 23, 2017 (2 pages).

\* cited by examiner

ENDOSCOPIC REUSABLE SURGICAL DEVICE

CROSS-REFERENCE TO RELATED APPLICATIONS

This application is a National Stage Application of PCT/CN2017/077303 under 35USC § 371 (a), the disclosure of the above-identified application is hereby incorporated by reference in its entirety.

BACKGROUND

Technical Field

The present disclosure relates to reusable surgical devices and in particular to endoscopic reusable surgical devices having a reusable handle assembly and a reusable shaft assembly configured to be cleaned and/or sterilized.

Description of Related Art

Surgical devices, such as graspers, staplers, and surgical clip appliers are known in the art and are used in various surgical procedures. In laparoscopic surgical procedures, abdominal cavity is accessed through narrow tubes or cannulas inserted through an incision. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar. Some of these surgical instruments are reusable surgical devices.

After use, reusable surgical devices need to be cleaned and sterilized. Some surgical reusable devices are designed to be easily disassembled such that internal components of the reusable surgical devices can be cleaned by brushing and/or flushing with cleaning solutions. Other types of reusable surgical devices include liquid access ports, such as Luer lock connectors, for connecting fluid sources for flushing the surgical devices. However, such reusable devices need to be sealed prior to being reused. Accordingly there is a need for reusable surgical devices that are capable of being cleaned and/or sterilized while being resealable.

SUMMARY

According to one embodiment of the present disclosure, an endoscopic shaft assembly is disclosed. The endoscopic shaft assembly includes: an elongate shaft; and an outer housing coupled to a proximal portion of the elongate outer shaft. The outer housing includes: a tubular wall defining a cavity; and a shaft plunger disposed within the cavity and configured to move axially within at least a portion of the cavity along a travel path. The shaft plunger includes a collar. The collar is configured to be separated from the tubular wall along a first travel portion of the travel path and to contact the tubular wall along a second travel portion of the travel path.

According to one aspect of the above embodiment, the cavity includes a first cavity portion having a first diameter and a second portion having a second cavity diameter, the first cavity portion corresponding to the first travel portion and the second cavity portion corresponding to the second travel portion.

According to one aspect of the above embodiment, the first diameter is larger than the second diameter. The collar has an outer diameter that is substantially equal to the second diameter. The first cavity portion is disposed proximally of the second cavity portion.

According to another aspect of the above embodiment, the cavity includes a third cavity disposed distally of the second cavity portion. The third cavity is configured to prevent entry of the collar thereinto. The third cavity has a third diameter that is smaller than the second diameter and the outer diameter of the collar.

According to a further aspect of the above embodiment, the endoscopic shaft assembly further includes a biasing member disposed within the cavity, the biasing member configured to bias the shaft plunger in a distal direction. The biasing member, when in a relaxed state, is configured to maintain the shaft plunger at a distance such that the collar is disposed within the first cavity portion.

According to another embodiment of the present disclosure, a surgical device is disclosed. The surgical device includes: a handle assembly and an endoscopic shaft assembly configured to couple to the handle assembly. The endoscopic shaft assembly includes: an elongate outer shaft; and an outer housing coupled to a proximal portion of the elongate outer shaft. The outer housing includes: a tubular wall defining a cavity; a biasing member disposed within the cavity; and a shaft plunger including a collar and disposed within the cavity. The shaft plunger is configured to move axially within at least a portion of the cavity from a first position to a second position, such that in the first position the collar is separated from the tubular wall and in the second position the collar contacts the tubular wall.

According to one aspect of the above embodiment, the handle assembly includes a trigger and a drive plunger movable by the trigger. Upon the endoscopic shaft assembly being coupled to the handle assembly, the drive plunger engages the shaft plunger and moves the shaft plunger to the second position. The outer housing further includes a proximal opening in communication with the cavity, such that when the endoscopic shaft assembly is coupled to the handle assembly, the drive plunger passes through the proximal opening. Conversely, upon the endoscopic shaft assembly being detached from the handle assembly the biasing member moves the shaft plunger to the first position.

According to another aspect of the above embodiment, the collar includes a frustoconical portion that is separated from the proximal opening when the shaft plunger is in the first position thereby creating a passage for adding a sterilizing agent into the cavity.

According to a further aspect of the above embodiment, the outer housing further includes a tubular wall and a side opening therethrough in communication with the cavity.

According to one aspect of the above embodiment, the handle assembly includes a nose portion configured to couple to the outer housing, the nose portion includes a plug configured to seal the side opening upon the endoscopic shaft assembly being coupled to the handle assembly.

According to a further embodiment of the present disclosure, a method for sterilizing a surgical device is disclosed. The method includes: detaching an endoscopic shaft assembly from a handle assembly. The endoscopic assembly includes a tubular wall defining a cavity, a biasing member disposed within the cavity, and a shaft plunger having a collar and disposed within the cavity, wherein the biasing member moves the shaft plunger upon detaching the endoscopic shaft assembly from the handle assembly into a first position in which the collar is separated from the tubular wall thereby creating a passage through the cavity. The method further includes supplying a sterilizing agent into passage.

BRIEF DESCRIPTION OF THE DRAWINGS

A particular embodiment of a surgical device is disclosed herein with reference to the drawings wherein.

DETAILED DESCRIPTION OF EMBODIMENTS

Figure 1:
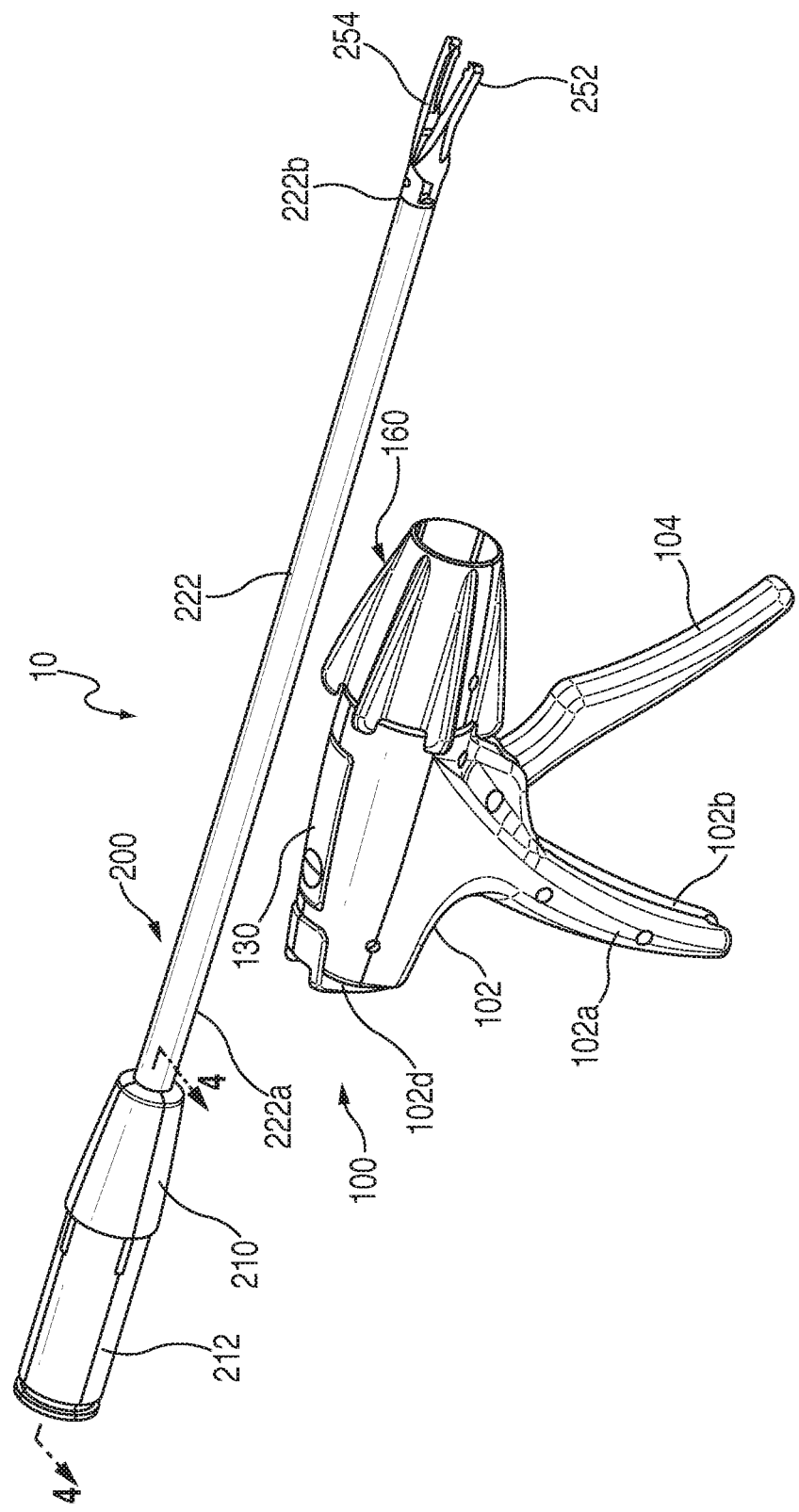
FIG. 1 is a perspective view of a reusable surgical device including a reusable handle assembly and an endoscopic shaft assembly selectively connectable to the handle assembly according to an embodiment of the present disclosure.

Embodiments of reusable surgical device, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

The present disclosure provides a reusable surgical device having a handle assembly and an endoscopic shaft assembly. The endoscopic shaft assembly includes an outer housing that is couplable to a handle assembly. The outer housing includes a shaft plunger movable therein that is configured to contact inner side walls of the outer housing when the endoscopic shaft assembly is connected to the handle assembly. When the endoscopic shaft assembly is disconnected from the handle assembly, the shaft plunger is moved axially in a proximal direction by a biasing member, such that the shaft plunger no longer contacts the inner side walls of the outer housing. As a result of this movement, a passage is opened into the outer housing and the endoscopic shaft assembly, allowing for introduction of a sterilization agent into the endoscopic shaft assembly.

Figure 2:
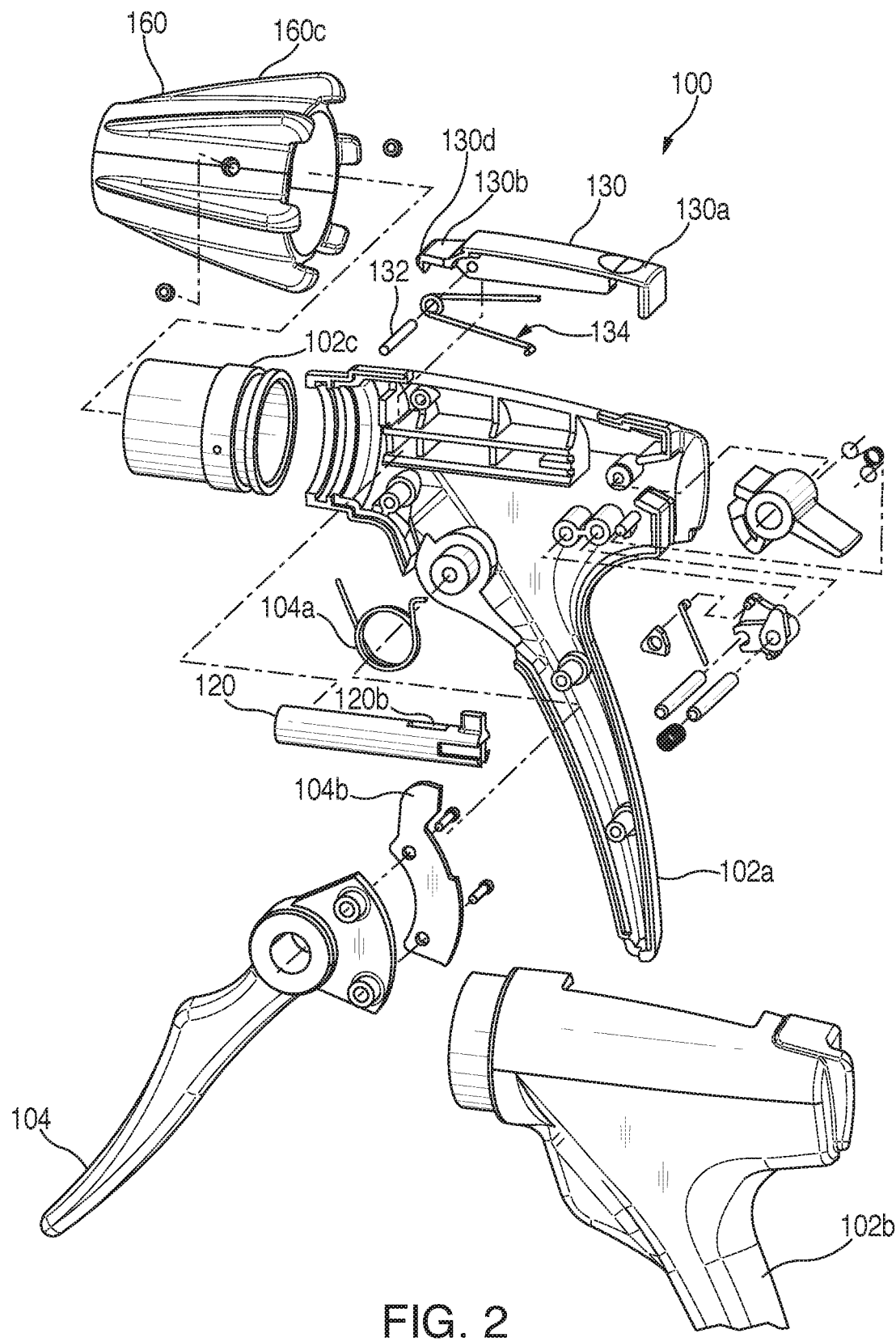
FIG. 2 is a perspective view of the handle assembly with parts disassembled.
Figure 3:
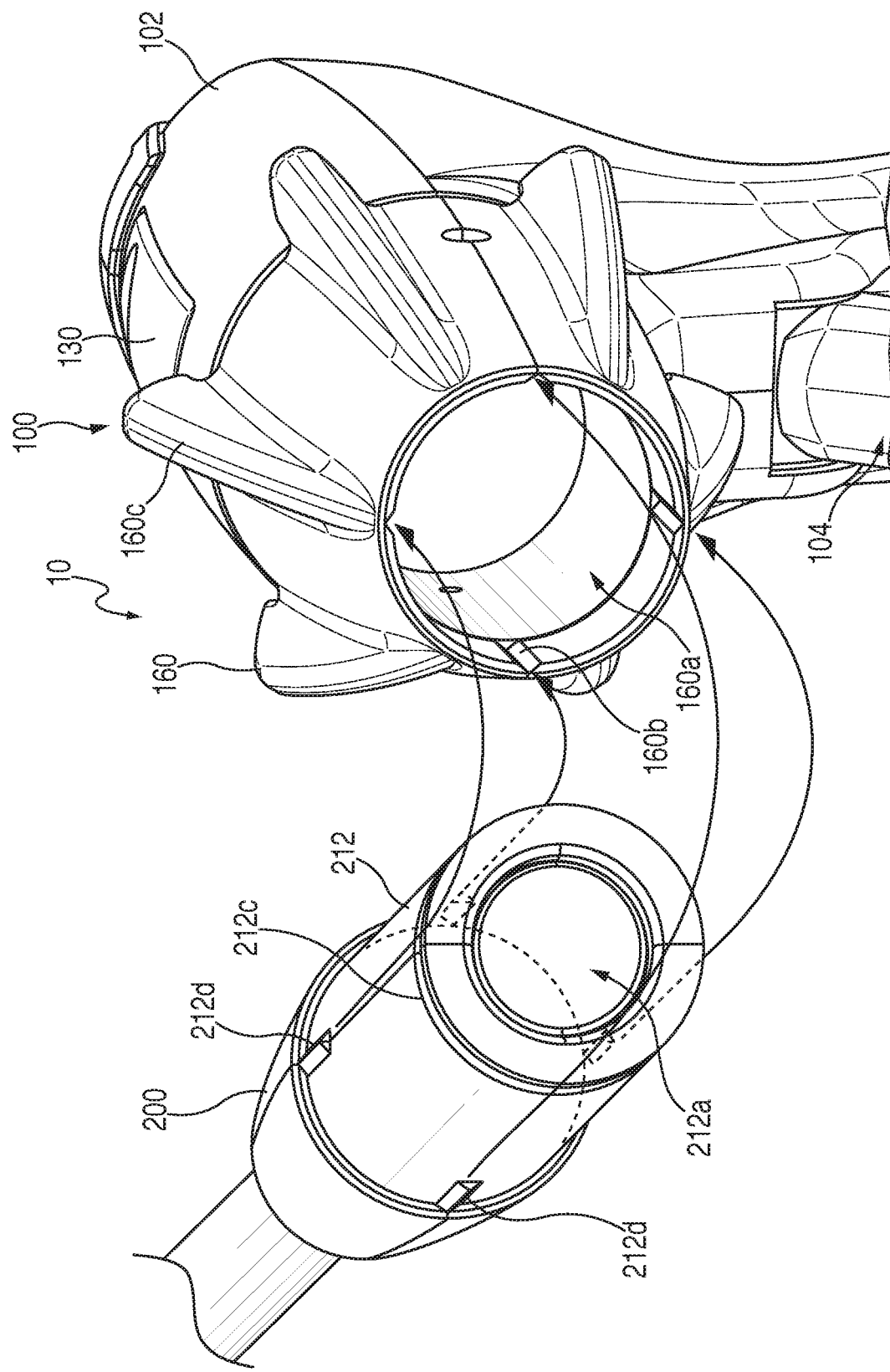
FIG. 3 is a perspective view illustrating connection of the endoscopic shaft assembly to the handle assembly.

Referring now to FIGS. 1-3, an endoscopic surgical device 10 includes a reusable handle assembly 100 and a reusable endoscopic shaft assembly 200, which is shown as a surgical clip applier. In embodiments, the endoscopic surgical device 10 is configured to couple to a plurality of endoscopic shaft assemblies 200 including, but not limited to, surgical graspers, staplers, clip appliers, and the like.

In accordance with the present disclosure, the endoscopic shaft assembly 200 may be configured to apply fasteners, e.g., surgical clips, staples, etc. The handle assembly 100 is configured to actuate the endoscopic shaft assembly 200 to grasp tissue and/or fire and form the fasteners loaded therein onto underlying tissue and/or vessels depending on the type of the endoscopic shaft assembly 200.

Referring now to FIGS. 1-3, handle assembly 100 of endoscopic surgical device 10 includes a housing 102 having a first half-section 102a and a second half-section 102b (FIG. 2). Housing 102 of handle assembly 100 further includes a nose portion 102c (FIG. 2). Housing 102 of handle assembly 100 may be formed any suitable materials, such as thermoplastics or metals.

Handle assembly 100 also includes a rotation knob 160 rotatably supported on nose portion 102c of housing 102. Rotation knob 160 includes a bore 160a having an annular array of longitudinally extending grooves 160b (FIG. 3) formed in a surface thereof. Grooves 160b of rotation knob 160 function as clocking and alignment features for the connection of endoscopic assembly 200 with handle assembly 100. Rotation knob 160 further includes a plurality of finger grip ribs 160c projecting from an outer surface thereof.

Handle assembly 100 further includes a trigger 104 pivotably supported between first half-section 102a and second half-section 102b of housing 102 (FIGS. 1 and 2). Trigger 104 is biased by a biasing member 104a (e.g., a return spring, compression spring or torsion spring) to an un-actuated condition. Trigger 104 includes a drive arm 104b extending therefrom. Drive arm 104b may be integrally formed therewith or may be separately and fixedly secured to trigger 104.

With reference to FIG. 2, handle assembly 100 includes a drive plunger 120 operatively connected to trigger 104. Specifically, drive plunger 120 is slidably supported within housing 102. Drive plunger 120 includes a proximally extending trigger slot 120b formed in a proximal portion thereof for operatively receiving the drive arm 104b of trigger 104 in order to distally advance drive plunger 120 during actuation of trigger 104.

The handle assembly 100 also includes a release lever 130 pivotally supported on and connected to housing 102 via a pivot pin 132. Pivot pin 132 is supported in housing 102. Release lever 130 includes a proximal end 130a extending proximally of pivot pin 132. Release lever 130 includes a distal end 130b extending distally of pivot pin 132. Distal end 130b of release lever 130 includes a catch 130d projecting therefrom, in a direction towards drive plunger 120. Catch 130d is located distally of drive plunger 120.

A biasing member 134, in the form of a leaf spring, may be provided which tends to bias distal end 130b and catch 130d of release lever 130 towards drive plunger 120 of handle assembly 100, and tends to bias proximal end 130a of release lever 130 upwardly. Specifically, biasing member 134 maintains catch 130d of release lever 130 in engagement with endoscopic shaft assembly 200.

With continued reference to FIGS. 1-3, endoscopic shaft assembly 200 includes a hub assembly 210, an elongate outer tube 222 extending from hub assembly 210 and a pair of jaws 252 and 254 pivotally connected to a distal end 222b of elongate outer tube 222. The elongate outer tube 222 may have any suitable outer diameter (e.g., about 5 mm or about 10 mm) and length depending on intended use. In one embodiment, the elongate outer tube 222 may have a length of from about 30 cm to about 40 cm.

Hub assembly 210 is configured for selective connection to rotation knob 160 and nose portion 102c of housing 102 of handle assembly 100 (FIGS. 2 and 3). Hub assembly 210 includes an outer housing 212 having a tubular (e.g., cylindrical or any other suitable cross-section) outer profile and defines an outer annular channel 212c formed in an outer surface thereof, and one or more axially extending ribs 212d projecting from an outer surface thereof. Outer annular channel 212c of outer housing 212 is configured to receive catch 130d of release lever 130 of handle assembly 100 when endoscopic shaft assembly 200 is coupled to handle assembly 100. Outer housing 212 of hub assembly 210 further defines a proximal opening 212a configured to slidably receive a distal end of drive plunger 120 of handle assembly 100, when endoscopic shaft assembly 200 is coupled to handle assembly 100.

Ribs 212d of outer housing 212 act as alignment features during connection of endoscopic shaft assembly 200 and handle assembly 100 with one another, wherein ribs 212d of outer housing 212 of endoscopic shaft assembly 200 are radially and axially aligned with respective grooves 160b of rotation knob 160 of handle assembly 100. During connection of endoscopic shaft assembly 200 and handle assembly 100, ribs 212d of outer housing 212 of endoscopic shaft assembly 200 are slidably received in respective grooves 160b of rotation knob 160 of handle assembly 100 as the outer housing 212 is inserted into bore 160a of the rotation knob 160.

The connection of hub assembly 210 of endoscopic assembly 200 with rotation knob 160 of handle assembly 100 enables endoscopic assembly 200 to rotate 360°, about a longitudinal axis thereof, relative to handle assembly 100. In particular, the hub assembly 210 of the endoscopic assembly 200 is rotationally secured to the rotation knob 160 by the interlocking of the ribs 212b with the grooves 160b allowing for rotation of the hub assembly 210 within the bore 160a.

Figure 4:
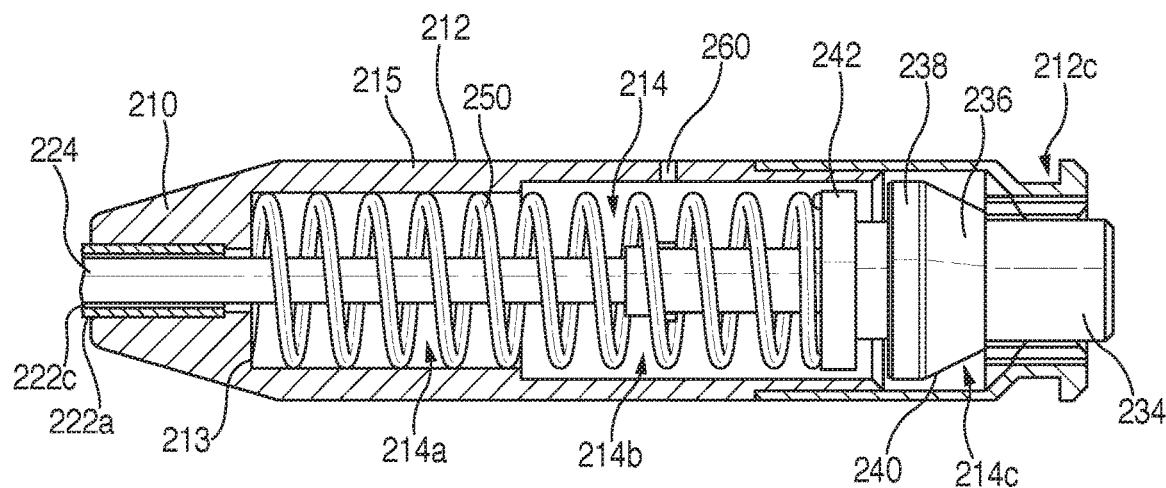
FIG. 4 is a side, cross-sectional view of a proximal portion of the endoscopic shaft assembly taken along section line "4-4" being disconnected from the handle assembly according to one embodiment of the present disclosure.
Figure 5:
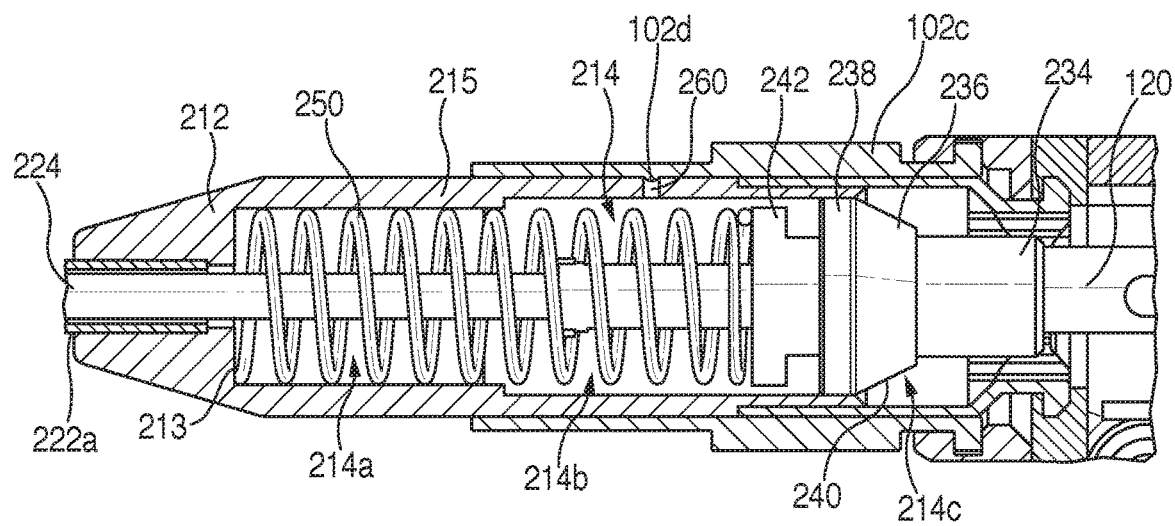
FIG. 5 is a cross-sectional view of the proximal portion of the endoscopic shaft assembly of FIG. 4 being connected to the handle assembly.
Figure 6:
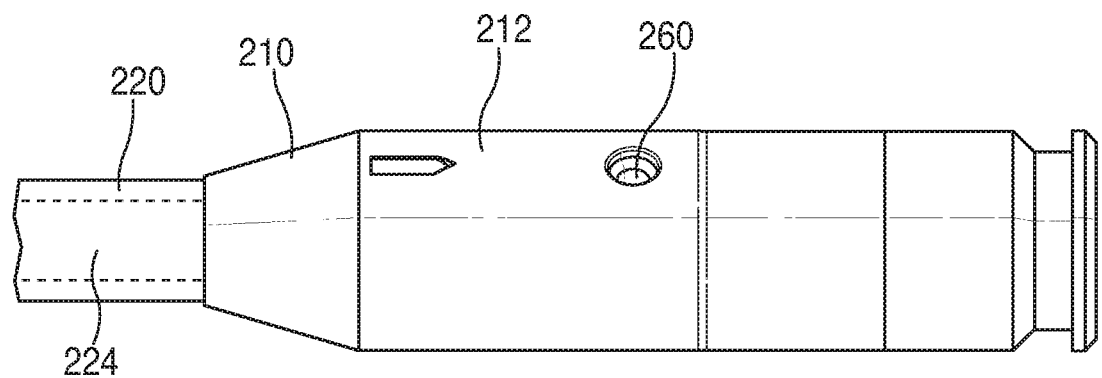
FIG. 6 is a side view of the proximal portion of the endoscopic shaft assembly according to another embodiment of the present disclosure.

With reference to FIGS. 4 and 5, the elongate outer tube 222 of the endoscopic shaft assembly 200 extends distally from hub assembly 210. Elongate outer tube 222 includes a proximal end 222a supported and secured to outer housing 212 of hub assembly 210, a distal end 222b (FIG. 1), and a lumen 222c extending longitudinally through the elongate outer tube 222. Elongate outer tube 222 further includes an inner shaft 224 slidably supported within lumen 222c of outer tube 222. The inner shaft 224 is actuatable by the trigger 224 and is configured to actuate the jaws 252 and 254 as described in further detail below.

The outer housing 212 includes a distal wall 213 and a tubular wall 215 extending proximally from the distal wall 213 and defining a cavity 214. The cavity 214 also includes a distal portion 214a connected to the lumen 222c of the elongate outer tube 222 such that a proximal end 224a of the inner shaft 224 extends proximally past proximal end 222a of outer tube 222 and is disposed within the cavity 214. The cavity 214 also includes a middle portion 214b and a proximal portion 214c connected to the proximal opening 212a.

Hub assembly 210 includes a shaft plunger 234 slidably supported within the cavity 214. Shaft plunger 234 is fixedly coupled to the proximal end 224a of the inner shaft 224. Shaft plunger 234 is sized and configured for slidable receipt within the cavity 214. The shaft plunger 234 includes a collar 236 which is shown being disposed about a middle portion of the plunger 234. In embodiments, the collar 236 may be located along any portion of the plunger 234. The collar 236 may be integrally formed with the plunger 234 or alternatively, may be coupled to the plunger 234 using any suitable methods, such as welding, adhesives, fasteners, and the like. The collar 236 has a base 238 and a frustoconical portion 240 extending proximally from the base 238. As used herein, the term "frustoconical" denotes a cone whose tip has been truncated by a plane parallel to the cone's base.

Hub assembly 210 includes a biasing member 250 (e.g., a compression spring) disposed within the cavity 214. Specifically, biasing member 250 is interposed between the distal wall 213 of outer housing 212 and a proximal surface of shaft plunger 234. In embodiments, the shaft plunger 234 may include a second collar 242 configured to contact a proximal end of the biasing member 250. In further embodiments, the proximal end of the biasing member 250 may contact the base 238 of the collar 236 directly. The biasing member 250 pushes the shaft plunger 234 in the proximal direction, and in its relaxed state, the biasing member 250 maintains the collar 236 within the proximal portion 214c of the cavity 214.

As described above, the endoscopic shaft assembly 200 is configured to selectively couple to the handle assembly 100. In order to couple the endoscopic shaft assembly 200 to the handle assembly 100, the release lever 130 is depressed into its unlocked configuration, which moves the catch 130d away from bore 160a. This allows for insertion of the outer housing 212 into bore 160a of the rotation knob 160. Thereafter, the release lever 130 is returned to its locked configuration, such that catch 130d of release lever 130 engages outer annular channel 212c of outer housing 212 of endoscopic shaft assembly 200. Concurrently, the drive plunger 120 also engages the shaft plunger 234 pushing the shaft plunger 234 distally as shown in FIG. 5. Thus, as the trigger 104 is actuated, the driver plunger 120 pushes the shaft plunger 234 in a distal direction to actuate the endoscopic shaft assembly 200, e.g., to actuate the pair of jaws 252 and 254.

The endoscopic shaft assembly 200 is configured to be cleaned and/or sterilized when decoupled from the handle assembly 100. This is accomplished due to a unique configuration of the cavity 214, the shaft plunger 234, and the biasing member 250. The distal, proximal, and middle portions 214a, 214b, 214c have progressively increasing inner diameters, from distal to proximal portions 214a and 214c. In particular, the distal portion 214a has a first diameter, which is the smallest of the three diameters of the cavity 214 and is dimensioned to be smaller than a diameter of second collar 242 and/or the base 238 of the collar 236. Thus, second collar 242 and/or the collar 236 cannot move distally into the distal portion 214a of the cavity 214. This limits travel distance of the shaft plunger 234 in the distal direction.

The middle portion 214b has an inner diameter that is larger than the diameter of the distal portion 214a. In particular, the inner diameter of the middle portion 214b is substantially equal to the outer diameter of the base 238 of the collar 236, such that the second collar 242 and/or the base 238 of the collar 236 fit within the middle portion 214b. This configuration allows for movement of the base 238 of the collar 236 through the middle portion 214b, while simultaneously sealing the middle portion 214b and the distal portion 214a, as well as egress into the lumen 222c of the elongate outer tube 222.

During use, the drive plunger 120 of the handle assembly 100 engages the shaft plunger 234 pushing the plunger 234 in the proximal direction as shown in FIG. 5. As a result, the collar 236 is moved proximally into the middle portion 214b and contacts the tubular wall 215 of the middle portion 214b as described above.

The proximal portion 214c has an inner diameter that is larger than the inner diameter of the middle portion 214b, such that the collar 236 is configured to move through the proximal portion 214c with a gap between the collar 236 and the tubular wall 215 of the proximal portion 214c. As described above, the biasing member 250 moves the shaft plunger 234 in the proximal direction such that the collar 236 is within the proximal portion 214c of the cavity 214 and is spaced from the tubular wall 215 by the gap. This location of the collar 236 within the proximal portion 214c creates a passage through the cavity 214 and allows for flushing the cavity 214 and the lumen 222c with cleaning and/or sterilization solutions and agents.

Suitable sterilization agents include solutions and mixtures of hydrogen peroxide, peracetic acid, glutaraldehyde, ortho-phthalaldehyde, and the like. The sterilizing agents may be injected into the endoscopic shaft assembly 200. In embodiments, the endoscopic shaft assembly 200 may be submerged into a vat of the sterilizing agent allowing the sterilizing agent to flow through the endoscopic shaft assembly 200, namely the cavity 214 and the lumen 222c.

In order to sterilize the endoscopic shaft assembly 200, the endoscopic shaft assembly 200 is disconnected from the handle assembly 100 by pressing on release lever 130 and pulling out, e.g., in a distal direction, the endoscopic shaft assembly 200. As the endoscopic shaft assembly 200 is disconnected, the biasing member 250 pushes the shaft plunger 234 in a proximal direction, moving the collar 236 into the proximal portion 214c of the cavity 214 as shown in FIG. 4. More specifically, the frustoconical portion 240 of the collar 236 allows for sterilization agent to be supplied into the endoscopic shaft assembly 200 through the opening 212a, into the proximal portion 214c and the cavity 214 and the lumen 222c. In particular, the frustoconical portion 240 does not occlude the opening 212a allowing for supply of the sterilization agent through the gap between the collar 236 and the tubular wall 215.

With reference to FIGS. 4-7, the endoscopic shaft assembly 200 includes an opening 260 on a side of the outer housing 212. The opening 260 is defined in the tubular wall 215 and is connected to the cavity 214. Thus, when the endoscopic shaft assembly 200 is disconnected from the handle assembly 100 the sterilization agent can also be supplied into the cavity 214 through the opening 260.

Figure 7:
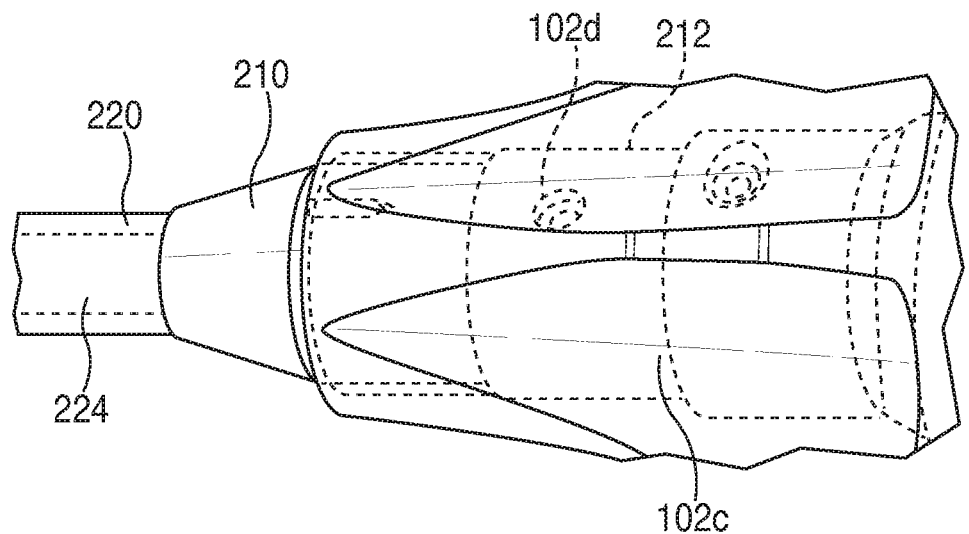
FIG. 7 is a side, partially-transparent view of the proximal portion of the endoscopic shaft assembly of FIG. 6 connected to the handle assembly.

The opening 260 is configured to be sealed by the nose portion 102c when the endoscopic shaft assembly 200 is coupled to the handle assembly 100. In particular, the nose portion 102c includes a plug 102d (FIGS. 5 and 7). The plug 102d may be a metal ferrule or another protrusion formed from any suitable material, such as thermoplastics, elastomers, and the like. Thus, once the endoscopic shaft assembly 200 is coupled to the handle assembly 100 the outer housing 212 of the endoscopic shaft assembly 200 is inserted into the nose portion 102c, the plug 102d engages and seals the opening 260. The engagement of the plug 102d with the opening 260 seals the cavity 214 ensuring that air and/or fluid leakage is within acceptable limits.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An endoscopic shaft assembly, comprising:
   an elongate shaft; and
   an outer housing coupled to a proximal portion of the elongate outer shaft, the outer housing including:
      a tubular wall defining a cavity; and
      a shaft plunger disposed within the cavity and configured to move axially within at least a portion of the cavity along a travel path, the shaft plunger including a collar, wherein the collar is configured to be separated from the tubular wall along a first travel portion of the travel path and to contact the tubular wall along a second travel portion of the travel path.

2. The endoscopic shaft assembly according to claim 1, wherein the cavity includes a first cavity portion having a first diameter and a second portion having a second cavity diameter, the first cavity portion corresponding to the first travel portion and the second cavity portion corresponding to the second travel portion.

3. The endoscopic shaft assembly according to claim 2, wherein the first diameter is larger than the second diameter.

4. The endoscopic shaft assembly according to claim 3, wherein the collar has an outer diameter that is substantially equal to the second diameter.

5. The endoscopic shaft assembly according to claim 4, wherein the first cavity portion is disposed proximally of the second cavity portion.

6. The endoscopic shaft assembly according to claim 5, wherein the cavity includes a third cavity disposed distally of the second cavity portion.

7. The endoscopic shaft assembly according to claim 6, wherein the third cavity is configured to prevent entry of the collar thereinto.

8. The endoscopic shaft assembly according to claim 7, wherein the third cavity has a third diameter that is smaller than the second diameter and the outer diameter of the collar.

9. The endoscopic shaft assembly according to claim 2, further comprising:
   a biasing member disposed within the cavity, the biasing member configured to bias the shaft plunger in a distal direction.

10. The endoscopic shaft assembly according to claim 9, wherein the biasing member in a relaxed state is configured to maintain the shaft plunger at a distance such that the collar is disposed within the first cavity portion.

11. A surgical device comprising:
    a handle assembly; and
    an endoscopic shaft assembly configured to couple to the handle assembly, the endoscopic shaft assembly, including:
       an elongate outer shaft; and
       an outer housing coupled to a proximal portion of the elongate outer shaft, the outer housing including:
          a tubular wall defining a cavity;
          a biasing member disposed within the cavity; and
          a shaft plunger including a collar and disposed within the cavity, wherein the shaft plunger is configured to move axially within at least a portion of the cavity from a first position to a second position, such that in the first position the collar is separated from the tubular wall and in the second position the collar contacts the tubular wall.

12. The surgical device according to claim 11, wherein the handle assembly includes a trigger and a drive plunger movable by the trigger.

13. The surgical device according to claim 12, wherein upon the endoscopic shaft assembly being coupled to the handle assembly, the drive plunger engages the shaft plunger and moves the shaft plunger to the second position.

14. The surgical device according to claim 13, wherein the outer housing further includes a proximal opening in communication with the cavity, such that wherein upon the endoscopic shaft assembly being coupled to the handle assembly, the drive plunger passes through the proximal opening.

15. The surgical device according to claim 14, wherein upon the endoscopic shaft assembly being detached from the handle assembly the biasing member moves the shaft plunger to the first position.

16. The surgical device according to claim 15, wherein the collar includes a frustoconical portion that is separated from the proximal opening when the shaft plunger is in the first position thereby creating a passage for adding a sterilizing agent into the cavity.

17. The surgical device according to claim 15, wherein the handle assembly includes a nose portion configured to couple to the outer housing, the nose portion includes a plug configured to seal the side opening upon the endoscopic shaft assembly being coupled to the handle assembly.

18. The surgical device according to claim 11, wherein the outer housing further includes a tubular wall and a side opening therethrough in communication with the cavity.

19. A method for sterilizing a surgical device, the method comprising:
   detaching an endoscopic shaft assembly from a handle assembly, the endoscopic assembly including a tubular wall defining a cavity, a biasing member disposed within the cavity, and a shaft plunger having a collar and disposed within the cavity, wherein the biasing member moves the shaft plunger upon detaching the endoscopic shaft assembly from the handle assembly into a first position in which the collar is separated from the tubular wall thereby creating a passage through the cavity; and
   supplying a sterilizing agent into passage.

* * * * *